(12) United States Patent
Aharoni et al.

(10) Patent No.: US 9,342,789 B2
(45) Date of Patent: *May 17, 2016

(54) CLASSIFICATION RELIABILITY PREDICTION

(71) Applicant: International Business Machines Corporation, Armonk, NY (US)

(72) Inventors: Ehud Aharoni, Kfar Saba (IL); Ruty Rinott, Jerusalem (IL); Noam Slonim, Jerusalem (IL)

(73) Assignee: International Business Machines Corporation, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/729,080

(22) Filed: Jun. 3, 2015

(65) Prior Publication Data

US 2015/0262070 A1    Sep. 17, 2015

Related U.S. Application Data

(63) Continuation of application No. 13/400,070, filed on Feb. 19, 2012, now Pat. No. 9,087,303.

(51) Int. Cl.

| | |
|---|---|
| *G06F 15/18* | (2006.01) |
| *G06N 5/04* | (2006.01) |
| *G06Q 10/10* | (2012.01) |
| *G06Q 50/24* | (2012.01) |
| *G06N 99/00* | (2010.01) |
| *G06F 17/30* | (2006.01) |
| *G06K 9/62* | (2006.01) |

(52) U.S. Cl.
CPC .......... *G06N 5/048* (2013.01); *G06F 17/30705* (2013.01); *G06K 9/6265* (2013.01); *G06N 99/005* (2013.01); *G06Q 10/10* (2013.01); *G06Q 50/24* (2013.01)

(58) Field of Classification Search
None
See application file for complete search history.

(56) References Cited

U.S. PATENT DOCUMENTS

| | | | |
|---|---|---|---|
| 7,107,254 | B1 | 9/2006 | Dumais et al. |
| 7,512,496 | B2 | 3/2009 | Shams et al. |
| 7,577,709 | B1 | 8/2009 | Kolcz |
| 2006/0179019 | A1 | 8/2006 | Bradski |
| 2009/0182696 | A1 | 7/2009 | Menahem et al. |
| 2011/0106734 | A1 | 5/2011 | Boult et al. |

OTHER PUBLICATIONS

Seewald et al., "An Evaluation of Grading Classifiers", Proceedings of the 4th International Conference on Advances in Intelligent Data Analysis, vol. 2189/2001, pp. 115-124, Jan. 1, 2001.

*Primary Examiner* — Kakali Chaki
*Assistant Examiner* — Mai T Tran
(74) *Attorney, Agent, or Firm* — Ziv Glazberg

(57) ABSTRACT

A method, apparatus and product useful for classification reliability prediction. The method being a computer-implemented method performed by a processor, the method comprising: obtaining a prediction of a label for a dataset made by a classifier tool, wherein the classifier tool is aimed at predicting the label based on a classification model and in view of a set of features defining the dataset; obtaining a reliability prediction of a reliability label relating to the prediction of the classifier tool based on a reliability classifier tool, wherein the reliability classifier tool is aimed at predicting the reliability label based on a classification model and in view of a second set of features; and outputting to a user the label prediction and an associated reliability prediction.

9 Claims, 4 Drawing Sheets

US 9,342,789 B2

CLASSIFICATION RELIABILITY PREDICTION

CROSS-REFERENCE TO RELATED APPLICATIONS

The present application is a continuation and claims the benefit of U.S. non-provisional application Ser. No. 13/400,070 filed on 19 Feb. 2012, which is hereby incorporated by reference in its entirety.

TECHNICAL FIELD

The present disclosure relates generally to machine learning and, more particularly to estimating reliability of a prediction provided based on a classification algorithm.

BACKGROUND

As is known in the art, machine learning techniques may be utilized to make a prediction with respect to given data. Generally, a classification algorithm is a method in which training dataset is provided to the algorithm and utilized for learning. After a training phase, the classification algorithm may be adapted to the specific problem at hand and may be able to predict information with respect to new, optionally unseen, instances.

The training data may comprise a sample of data-points, each given using a set of features which are used by the classifier, as well as the label, which is to be predicted. As an example, in case a gender of a person is predicted, the features may be height, age, weight and first name. It will be noted that in some cases, some features are useful for the prediction while others may not be useful. In this example, in addition to the features, a gender label is given for each data-point, so as to enable the classifier to learn how to predict such information for new data-points.

After the training phase is concluded, features of data-points are given and the classifier may determine a predicted label. In some cases, feedback may be given to indicate to the classifier whether the prediction was correct.

BRIEF SUMMARY

One exemplary embodiment of the disclosed subject matter is a computer-implemented method performed by a processor, the method comprising: obtaining a prediction of a label for a dataset made by a classifier tool, wherein the classifier tool is aimed at predicting the label based on a classification model and in view of a set of features defining the dataset; obtaining a reliability prediction of a reliability label relating to the prediction of the classifier tool based on a reliability classifier tool, wherein the reliability classifier tool is aimed at predicting the reliability label based on a classification model and in view of a second set of features; and outputting to a user the label prediction and an associated reliability prediction.

Another exemplary embodiment of the disclosed subject matter is a computerized apparatus having a processor, the processor being adapted to perform the steps of: obtaining a prediction of a label for a dataset made by a classifier tool, wherein the classifier tool is aimed at predicting the label based on a classification model and in view of a set of features defining the dataset; obtaining a reliability prediction of a reliability label relating to the prediction of the classifier tool based on a reliability classifier tool, wherein the reliability classifier tool is aimed at predicting the reliability label based on a classification model and in view of a second set of features; and outputting to a user the label prediction and an associated reliability prediction.

Yet another exemplary embodiment of the disclosed subject matter is a computer program product comprising: a non-transitory computer readable medium retaining program instructions, which instructions when read by a processor, case the processor to performs the steps of: obtaining a prediction of a label for a dataset made by a classifier tool, wherein the classifier tool is aimed at predicting the label based on a classification model and in view of a set of features defining the dataset; obtaining a reliability prediction of a reliability label relating to the prediction of the classifier tool based on a reliability classifier tool, wherein the reliability classifier tool is aimed at predicting the reliability label based on a classification model and in view of a second set of features; and outputting to a user the label prediction and an associated reliability prediction.

BRIEF DESCRIPTION OF THE SEVERAL VIEWS OF THE DRAWINGS

The present disclosed subject matter will be understood and appreciated more fully from the following detailed description taken in conjunction with the drawings in which corresponding or like numerals or characters indicate corresponding or like components. Unless indicated otherwise, the drawings provide exemplary embodiments or aspects of the disclosure and do not limit the scope of the disclosure. In the drawings.

DETAILED DESCRIPTION

Figure 1:
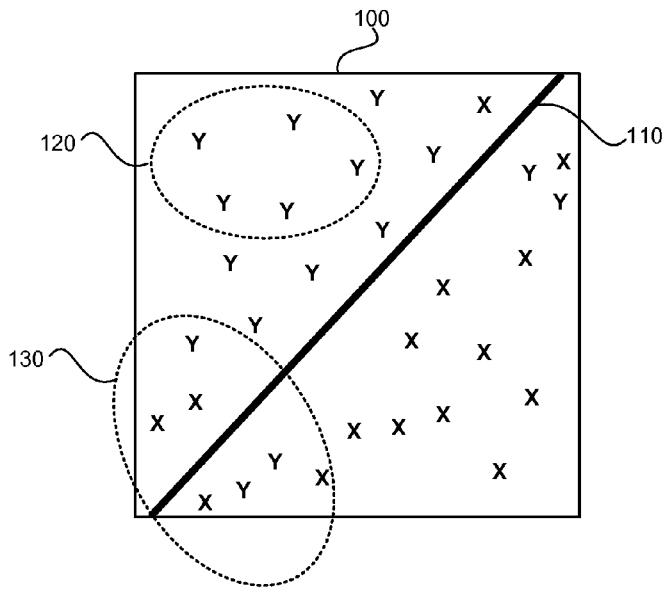
FIG. 1 showing an illustration of a population of data-points, given using two features, in accordance with some exemplary embodiments of the disclosed subject matter.

The disclosed subject matter is described below with reference to flowchart illustrations and/or block diagrams of methods, apparatus (systems) and computer program products according to embodiments of the subject matter. It will be understood that blocks of the flowchart illustrations and/or block diagrams, and combinations of blocks in the flowchart illustrations and/or block diagrams, can be implemented by computer program instructions. These computer program instructions may be provided to one or more processors of a general purpose computer, special purpose computer, a tested processor, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a non-transient computer-readable medium that can direct a computer or other programmable data processing apparatus to function in a particular manner, such that the instructions stored in the non-transient computer-readable medium produce an article of manufacture including instruction means which implement the function/act specified in the flowchart and/or block diagram block or blocks.

The computer program instructions may also be loaded onto a device. A computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the flowchart and/or block diagram block or blocks.

In the present disclosure a "classifier tool" is an apparatus, implemented in software, firmware, hardware, combination thereof, or the like, capable of utilizing a classification algorithm in order to provide a predication. It will be understood that the classifier tool may provide classification into discrete sets of labels (e.g., using classifier algorithms such as naïve-base, k-nearest neighbors, support vector machines, decision-trees, linear classification, or the like). Additionally or alternatively, the classifier tool may provide continuous output (e.g., continuous classification algorithms such as linear regression, logistic regression, Lasso algorithm, LOESS, and the like).

One technical problem dealt with by the disclosed subject matter is to estimate reliability associated with a prediction made by a classifier tool. Estimating reliability associated with each prediction and identifying unreliable prediction may be of great importance in various scenarios. For example, in clinical decision support systems which try to predict the best treatment, identifying unreliable predictions may assist the user to avoid wrong decisions.

One technical solution is to utilize a separate classifier tool, referred to as a reliability classifier tool or RCT, in order to predict reliability of a prediction made by the classifier tool. The RCT may aim to distinguish instances for which the predictions generated by the classifier tool were reliable, from instances for which the generated predictions were not reliable.

Another technical solution is to introduce additional features that were not used by the classifier tool itself, and which may be informative about reliability. Additionally or alternatively, the additional features may not be useful for performing the prediction itself, while still useful for predicting reliability. In some exemplary embodiments, the additional features may be by-products of the original classification operation, and may thus not be available to the classifier tool itself.

In some exemplary embodiments, the RCT and the original classifier tool, also referred to as CT, may utilize different classification algorithms.

Yet another technical solution is to provide a training scheme for training the RCT. In some exemplary embodiments, training the RCT may be based on a plurality of predictions with respect to the same data-point. A stability scheme may be aimed at determining reliability for training dataset based on a stability of prediction in view of different training data for the CT. Additionally or alternatively, a correct fraction scheme may be aimed at determining reliability for training dataset based on a correct fraction of the predictions provided in view of different training data for the CT. In some exemplary embodiments, reliability indication may be provided based on a correct/incorrect determination of the prediction made by the CT with respect to the correct label, which may be given as part as the training set.

One technical effect is that the disclosed subject matter is domain general and can be used on top of any classification method. Further, there is no limitation on using one type of classifier for the original classification task, accompanied by a different classification algorithm employed as the RCT.

Another technical effect is, when utilizing different classification algorithms, being able to capture unreliability which is associated with different sources of unreliability. One source of unreliability may be an insufficiency of training dataset, such as utilizing a small sample or a non-representative sample during the training phase. Another source of unreliability may be inherent to the data, such as the case when there is stochastic behavior, at least with respect to the features utilized by the CT. Yet another source of unreliability may be an abstraction or modeling by the classification algorithm itself. Different sources of unreliability may have varying effects in different samples.

As an example, consider a classification task that involves classification of patients into sick and healthy, based on the results of blood tests. Now assume that the blood samples were analyzed in one of two different laboratories, one of which was contaminated, inserting noise into the blood test results. While the identity of the lab is irrelevant to classifying patient to sick and healthy, it can be used by the RCT to identify that predictions made for patients tested in the contaminated lab are less reliable. In this example, the source of unreliability is inherent to some of the data and the stochastic behavior may arise for some samples but not others.

As another example, the source of unreliability may be due to the modeling by the classification algorithm, as is exemplified using FIG. 1 hereinbelow. As can be appreciated, the source of unreliability applies only to certain region of the data-points population.

As yet another example, the source of unreliability may be due to insufficient training dataset, such as training the classifier using a small sample, using an non-representative sample, or the like.

Referring now to FIG. 1 showing an illustration of a population of data-points, given using two features. The CT may determine a linear separation between different labels. However, the inherent assumption of the classification algorithm that such a linear separation exists, may be untrue, as in the case of Population 100. As can be appreciated, no linear line can separate between label X and label Y instances. An Estimated Line 110 may be determined, however, Estimated Line 110 is most useful with respect to area 120 and less useful with respect to area 130 in which a determination based thereof may be unreliable.

In case the RCT is not limited to the assumptions of the CT, such as by employing different algorithm, modeling Population 100 using additional features, or the like, the RCT may be able to predict low reliability of prediction for data-points in area 130 and high reliability of prediction for data-points in area 120.

It will be noted that reliability prediction is different than a probability that the classifier is correct. In some exemplary embodiments, "reliability" may be a measure that provides information about the accuracy of a prediction made by the classifier in question compared to a random classifier (e.g. made by the same classifier that is trained over a randomly labeled training data).

It will be appreciated that FIG. 1 exemplifies that an assumption by the CT may cause reliability problems. FIG. 1 is provided as an example only and other classification algorithms may introduce through their modeling similar reliability problems.

As can be appreciated, a technical effect of some embodiments of the disclosed subject matter is thus that different sources of unreliability may be identified in an automatic manner.

Yet another technical effect of utilizing the disclosed subject matter is the ability to detect unreliability arising from features that are not useful in making the prediction, and therefore may not be available for the CT while performing the prediction itself. Consider, again, the lab example provided hereinabove. The identity of the lab is not useful in making the prediction, although it is useful in determining the reliability of the prediction. As another example, the percent of missing values for a certain instance may be determined as not useful for classification, although it may indeed be of importance when estimating reliability.

Figure 2A:
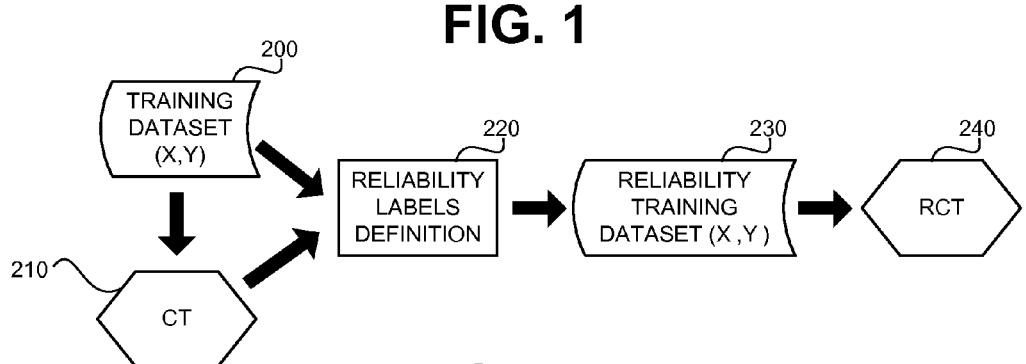
FIGS. 2A-2C show flowchart diagram of steps in methods for predicting prediction reliability, in accordance with some exemplary embodiments of the disclosed subject matter.

Referring now to FIG. 2A showing a flowchart diagram of steps in a method for training a RCT, in accordance with some exemplary embodiments of the disclosed subject matter.

A training dataset (200) is provided. The training dataset comprises features of data-points (X) and associated labeling thereof (Y). A CT 210 is provided with the training dataset (200) for training thereof. Based on reliability labels definition (220), such as stability scheme, correct fraction scheme, or the like, a reliability training dataset (230) may be determined. The reliability training dataset may comprise data-points given using different sets of features (X'), and associated labeling with respect to the reliability of prediction (Y), as determined in (220). RCT 240 may be provided the reliability training dataset of training.

In some exemplary embodiments, reliability labels definition (220) may comprise obtaining a prediction with respect to the dataset X by the CT 210. Based on the prediction, reliability indication may be determined.

In some exemplary embodiments, X and X' refer to the same instances, using a same set of features. Alternatively, X and X may refer to the same instances using different set of features, such that X' includes additional features, such as by-products of CT 210, features not useful in prediction but useful in reliability prediction, and the like. Additionally or alternatively, X may include features that are not includes in X'.

In some exemplary embodiments, CT 210 may be trained with respect to a first portion of the training dataset (X). Reliability labels definition (220) may be performed using a second portion of the training dataset (X), such as a different portion than the first portion. Thereby, based on a training of the CT 210 using the first portion, predictions on the second portion may be made and utilized in defining reliability labels (Y) useful in training RCT 240.

Figure 2B:
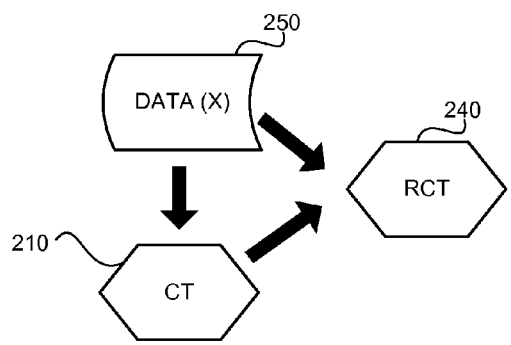

Referring now to FIG. 2B showing a flowchart diagram of steps in a method for performing predictions, in accordance with some exemplary embodiments of the disclosed subject matter.

Data-point X is provided (250) to CT 210, which provides a prediction of a suitable label thereof. RCT (240) is also provided the data-point, as well as the prediction and provides a reliability prediction regarding the prediction of CT 210. Additionally or alternatively, RCT 240 may be provided additional features that were not provided to CT 210, such as by-products of CT 210, features that are inconclusive regarding prediction made by CT 210, or the like.

Figure 2C:
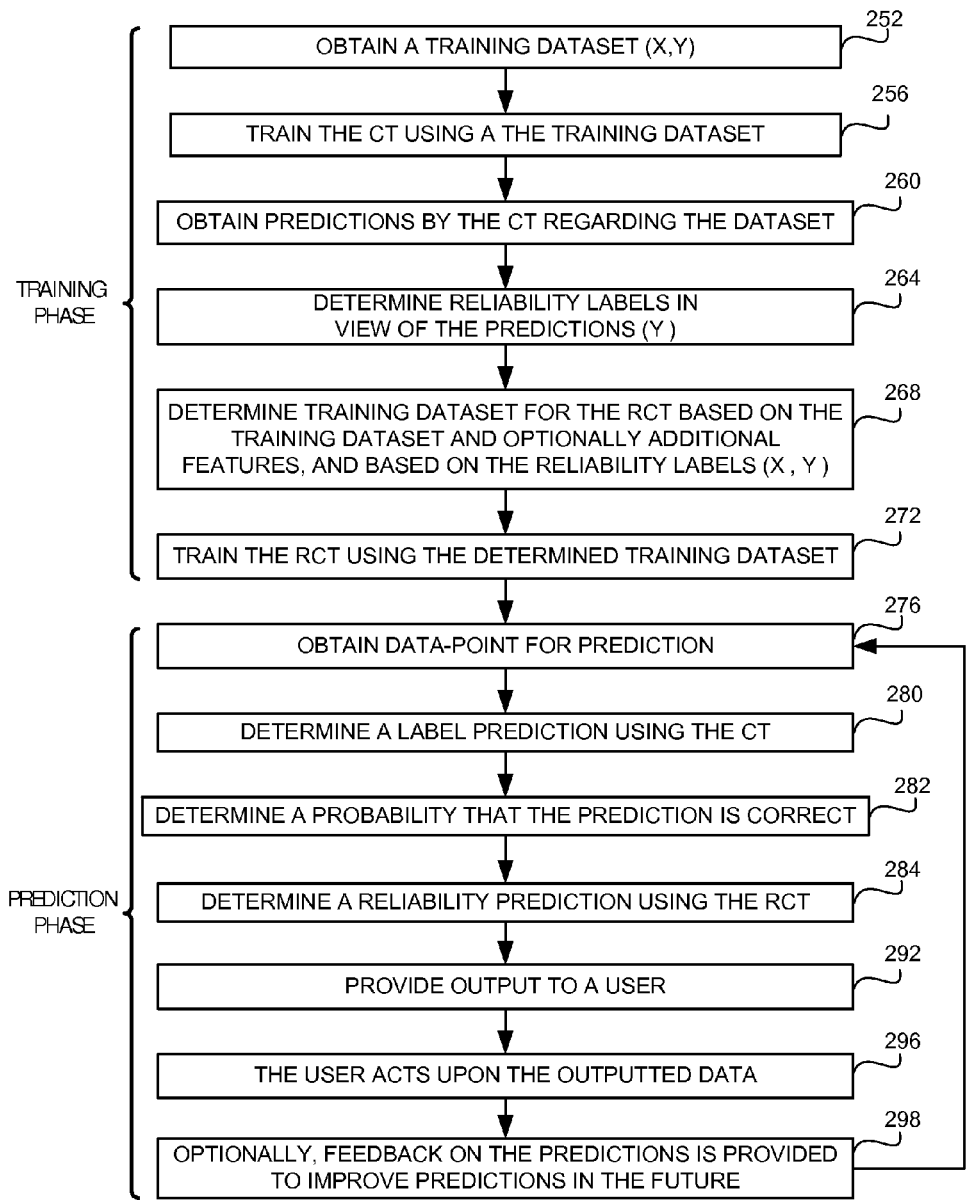

Referring now to FIG. 2C showing a flowchart diagram of steps in a method for training classifier tools and utilization thereof, in accordance with some exemplary embodiments of the disclosed subject matter. The method comprises a training phase (Steps 252-272) and a prediction phase, also referred to as a testing phase (Steps 276-298). The prediction phase may be performed repeatedly with respect to different data-points.

In Step 252, training dataset (X,Y) is obtained. The training dataset comprises a sample of data-points (i.e., x∈X) provided using a set of features (denoted F), and for each data-point an associated label is given (i.e., y∈Y: label(x)=y).

In Step 256, a CT, such as 210, may be trained using the training dataset. In some exemplary embodiments, only a portion of the dataset is utilized for training the CT, such that some data-points are not utilized for training the CT. Additionally or alternatively, the CT may require a subset of the set of features to define the data-points (i.e., $F_1 \subset F$) and accordingly only the subset of features with respect to the data-points may be provided to the CT.

In Step 260, predictions by the trained CT may be obtained. In some exemplary embodiments, the predictions may be with respect to data-points comprised by the training dataset. The data-points may or may not have been used for training the CT in Step 256.

In Step 264, reliability labels (Y) may be determined with respect to each predicted label of a data-point. The reliability label may be determined based on whether the prediction is correct (by comparing the predicted label with actual label y). Additionally or alternatively, the reliability label may be determined based on a plurality of predictions made with respect to the same data-point, such as in response to different training sessions. The stability of prediction may be measured by determining a dispersal factor of the predictions. As an example, a most commonly predicted label may be determined and a portion of predictions that predicted the commonly predicted label may be computed and used as a dispersal factor. Alternatively, statistical variance of the predictions may be computed and utilized as a dispersal factor. In some exemplary embodiments, the stability of prediction measurement may be computed and normalized to a number within a predetermined range. For example, a number between 0, indicating non-stable prediction, and 1, indicating stable and consistent prediction, thereby a reliability label may be determined for the prediction.

In some exemplary embodiments, a correct factor of the predictions may be computed. As opposed to stability, correct factor takes into account that there is a known correct label for the data-point. A portion of the predictions that were correct out of the total number of predictions may be computed and utilized to determine a reliability label. Additionally or alternatively, an orthogonal distance, or other computable differencing measurement, may be computed between the average, frequent or median prediction and the correct label. The distance may be utilized in determining the reliability labels (Y).

In step 268, training dataset (X') for the RCT, such as RCT 240, may be determined. The training dataset may be based on the dataset for which predictions were made in Step 260 and reliability labels were defined in Step 264. In some exemplary embodiments, the training dataset may further include features that were not part of the original training dataset obtained in Step 250, such as by-products generated during the prediction of Step 250. Additionally or alternatively, the training dataset X' may include features that were not utilized by the CT. I.e., the set of features may be $F_2 \subseteq F \cup \text{New Features}$, where F is the set of features that is provided in the training dataset and NewFeatures are features that were not originally provided and/or available such as by-products of the prediction process, the predicted label, and the like. In some exemplary embodiments, feature f∈F may be utilized for training the RCT and not the CT (i.e., $f \in F_2$, $f \notin F_1$), and vice versa.

Using the training dataset (X') and reliability labels (Y') the RCT may be trained in Step 272.

During the prediction phase, data-points are provided and a label prediction as well as a reliability prediction is provided. Optionally, a probability that the prediction is correct may be obtained as well and outputted.

In Step 276, a data-point is obtained for labeling prediction. The data-point may be provided using all features that are useful for the CT and RCT. Optionally, some features are generated automatically during the process, such as by-products of the CT prediction operation, and may not be provided upfront.

In Step 280, the CT may provide a label prediction for the data-point. In some exemplary embodiments, the data-point may be projected onto the space defined using $F_1$ and the projected data-point may be provided for the CT for prediction.

In some exemplary embodiments, optional Step 282 may determine probability of the prediction made by the CT to be correct. In some exemplary embodiments, the CT itself may provide such information. As opposed to reliability prediction, Step 282 provides a probability that the predication is correct. The probability may be a by-product provided by the CT itself.

In Step 284, the RCT may provide a reliability prediction for the data-point and predicted label. In some exemplary embodiments, the data-point provided in Step 276 may be projected onto the spaced defined by $F_2$ and additional features (e.g. NewFeautres) may be complemented automatically.

In Step 292, output may be provided to a user. The user may therefore be informed of the prediction and the reliability of such prediction. Additionally or alternatively, the user may also be informed of the probability that the prediction is correct. Based on the information provided to the user, the user may determine whether to accept the prediction, utilize a different prediction method, request for additional data to be used in the prediction, or take any other action based on the outputted data (Step 296). In some exemplary embodiments, some or all of the actions may be taken automatically based on predefined rules. In some exemplary embodiments, a proposed action may be suggested to the user, based upon the information.

Optionally, feedback to the CT and/or RCT may be provided in view of the predicted labels and/or reliability. As is known in the art, feedback to classifiers may be utilized to improve future predictions.

Figure 3A:
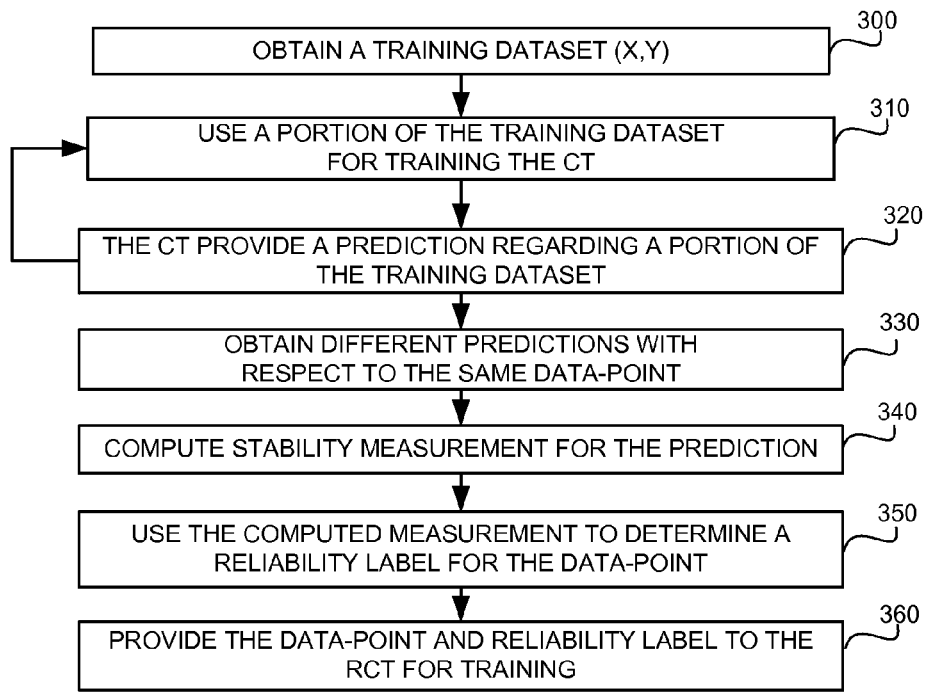
FIGS. 3A and 3B show flowchart diagrams of different training schemes, in accordance with some exemplary embodiments of the disclosed subject matter.

Referring now to FIG. 3A showing a flowchart diagram of a reliability prediction training scheme, in accordance with some exemplary embodiments of the disclosed subject matter. The method of FIG. 3A may be performed with respect to the training phase of FIG. 2C.

In Step 300, a training dataset (X,Y) is obtained.

In Step 310 a portion of the data-points comprised by the training dataset ($X_1 \subseteq X$) may be utilized to train the CT.

In Step 320, and in view of the training of the CT, the CT may provide predictions with respect to a portion of the data-points ($X_2 \subseteq X$).

It will be noted that $X_1$ and $X_2$ may be the same, may subsume one another, may be disjoint sets, may have some intersection, or have any other form of relationship therebetween. In some exemplary embodiments, the entire dataset may be utilized for both Steps 310 and 320. In some exemplary embodiments, a first portion may be utilized in Step 310 and a complementary portion may be utilized in Step 320.

Steps 310 and 320 may be performed a plurality of times, such as with respect to different training datasets during each training session. Learnt information may not be retained between training sessions, such as by initializing the CT between iterations. Additionally or alternatively, the learnt information may be retained, and thereby the CTs training dataset may be increased with each iteration.

After sufficient iterations Step 330 may be performed. Sufficiency of iterations may be determined, for example, when having at least a predetermined number of predictions with respect to the same data-point, after a predetermined number of iterations, or the like. In Step 330, the different predictions regarding the same data-point may be obtained.

In Step 340, a stability measurement may be computed for the data-point. As an example, the stability measurement may be $$S = \frac{CP}{N},$$

where CP is the common prediction and N is the number of predictions made. Referring still to this example, in case out of ten predictions seven are a prediction of label I, and the additional three predictions of one or more different labels, then the stability measurement may be 0.7. As another example, the stability measurement may be based on a variance computed based on the different labeling. In some exemplary embodiments, each label may be assigned a number in order to be able to compute a variance. The stability measurement may be, for example, a multiplicative inverse of the variance, thereby the lowest value indicates lowest stability of prediction and the highest possible stability of prediction (e.g., all predictions are the same and variance is zero) is the highest number. Other methods of computing stability measurements may be utilized in lieu of the aforementioned examples.

In Step 350, the computed measurement may be utilized to determine a reliability label for the data-point, and the reliability label may be utilized to train the RCT (Step 360).

In some exemplary embodiments, the training dataset may be utilized in whole to train the CT at any time after obtaining the different predictions (in the different iterations of step 320).

Figure 3B:
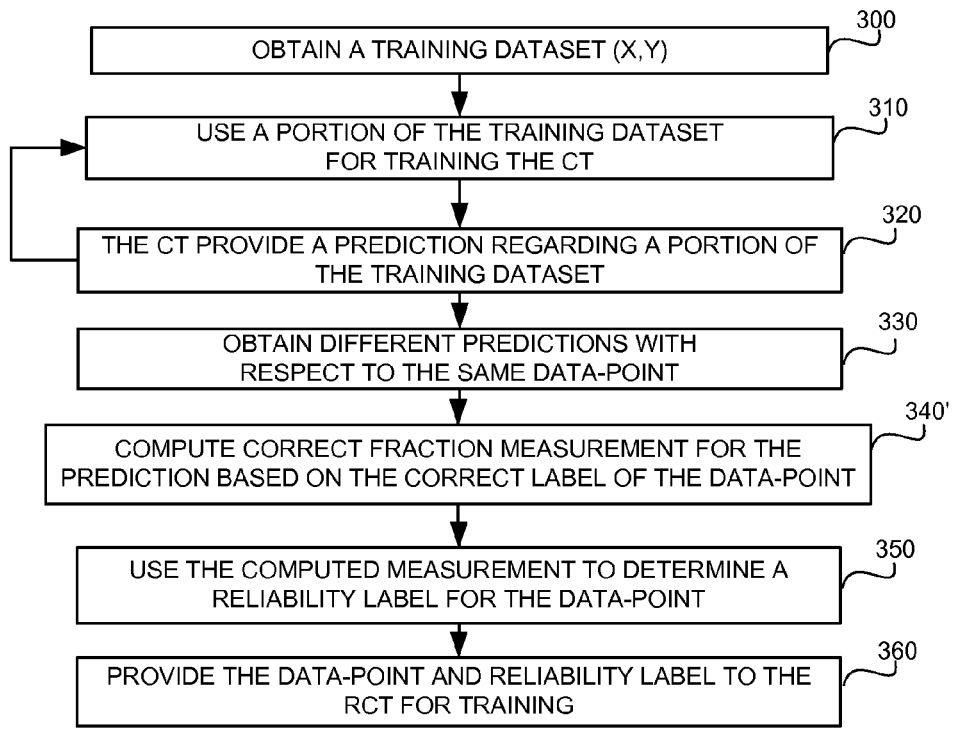

Referring now to FIG. 3B showing a flowchart diagram of a reliability prediction training scheme, in accordance with some exemplary embodiments of the disclosed subject matter, and similar to that depicted in FIG. 3A.

Instead of Step 340, step 340' may be performed, in which a correct fraction measurement is computed. As an example, the correct fraction measurement may be $$CF = \frac{L}{N},$$

where L is the label provided in the training dataset and N is the number of predictions made. Referring still to this example, in case out of ten predictions six are a prediction of the label that is given as the correct label in the training dataset, then the correct fraction measurement may be 0.6. Additionally or alternatively, the correct fraction may be measured using a computable distance between the average predicted label and the associated (correct) label in the training dataset.

It will be noted that in case that a single prediction is made with respect to the data-point, the correct fraction may be a binary indicative whether the prediction is correct.

Figure 4:
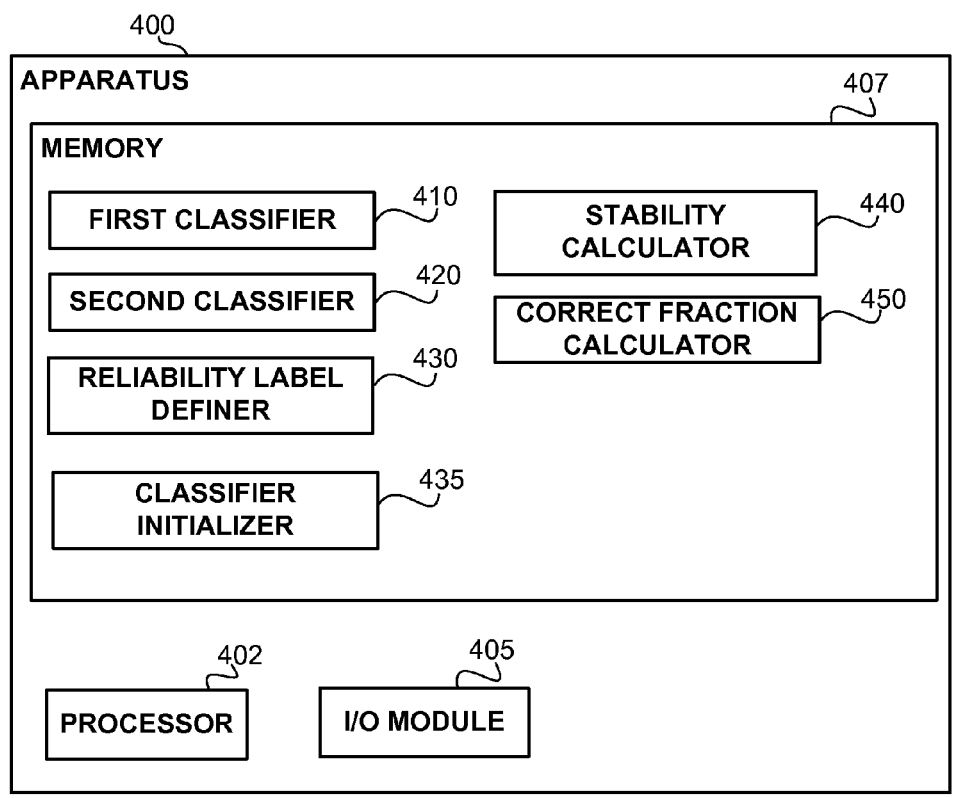
FIG. 4 shows a block diagram of components of a computerized apparatus, in accordance with some exemplary embodiments of the disclosed subject matter.

Referring now to FIG. 4 showing a block diagram of components of a computerized apparatus, in accordance with some exemplary embodiments of the disclosed subject matter.

In some exemplary embodiments, Apparatus 400 may comprise a Processor 402. Processor 402 may be a Central Processing Unit (CPU), a microprocessor, an electronic circuit, an Integrated Circuit (IC) or the like. Processor 402 may be utilized to perform computations required by Apparatus 400 or any of it subcomponents.

In some exemplary embodiments, Apparatus 400 may comprise an Input/Output (I/O) Module 405 such as a receiver, transmitter, transceiver, modem, an input device, an output device or the like. In some exemplary embodiments, I/O Module 405 is utilized to connect to an I/O device for providing input by or output to a human user. I/O Module 405 may be operatively connected to a display, to a pointing device, a keyboard, or the like. It will however be appreciated that the system can operate without human operation.

In some exemplary embodiments, Apparatus 400 may comprise a Memory 407. Memory 407 may be computerized memory, such as persistent or volatile, or a combination thereof. For example, Memory 407 can be a Flash disk, a Random Access Memory (RAM), a memory chip, an optical storage device such as a CD, a DVD, or a laser disk; a magnetic storage device such as a tape, a hard disk, storage area network (SAN), a network attached storage (NAS), or others; a semiconductor storage device such as Flash device, memory stick, or the like. In some exemplary embodiments, Memory 307 comprises several memory devices, such as for example a RAM and a hard disk. In some exemplary embodiments, Memory 407 may retain program code operative to cause Processor 402 to perform acts associated with any of the steps shown in FIG. 2A-2C, 3A-3B or the like.

The components detailed below may be implemented as one or more sets of interrelated computer instructions, executed for example by Processor 402 or by another processor. The components may be arranged as one or more executable files, dynamic libraries, static libraries, methods, functions, services, or the like, programmed in any programming language and under any computing environment.

In some exemplary embodiments, Memory 407 may comprise software-implemented classifiers (410 and 420) to be used as CT and RCT in accordance with the disclosed subject matter. In some exemplary embodiments, classifiers 410 420 may not be implemented using software and/or may be external to Apparatus 400.

Reliability Label Definer 430 may be configured to define a reliability label to be used during a training phase for training the RCT. Reliability Label Definer 430 may be configured to perform steps such as 264, 330, 340, 340', 350 or the like. In some exemplary embodiments, Reliability Label Definer 430 may be operatively coupled to Stability Calculator 440, Correct Fraction Calculator 450, or a similar calculator to be utilized for calculating a measurement useful in defining the reliability label.

In some exemplary embodiments, Classifier Initializer 435 may be configured to initialize a classifier, such as 410, so as to cause the classifier to drop previously learnt data. Classifier Initializer 435 may be utilized to cause training sessions of the CT to not retain learnt data, such as in-between repeating steps 310 and 320.

In some exemplary embodiments of the disclosed subject matter, two different classifiers may be trained. The first, CT, is aimed at solving the original classification problem, i.e., to predict the label associated with each test instance. The second classifier, RCT, may be aimed at predicting the reliability of the predictions made by CT. In some exemplary embodiments, RCT can be thought of as a function from X to $\{0, 1\}$, where $RCT(x)=1$ implies that $CT(x)$ should be considered "reliable" and $RCT(x)=0$ implies that $CT(x)$ should be considered "unreliable". The disclosed subject matter is not limited to the above-mentioned embodiment. As an example, different scores may be utilized to imply reliability and unreliability.

The flowchart and block diagrams in the figures illustrate the architecture, functionality, and operation of possible implementations of systems, methods and computer program products according to various embodiments of the present disclosure. In this regard, each block in the flowchart and some of the blocks in the block diagrams may represent a module, segment, or portion of program code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As will be appreciated by one skilled in the art, the disclosed subject matter may be embodied as a system, method or computer program product. Accordingly, the disclosed subject matter may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the present disclosure may take the form of a computer program product embodied in any tangible medium of expression having computer-usable program code embodied in the medium.

Any combination of one or more computer usable or computer readable medium(s) may be utilized. The computer-usable or computer-readable medium may be, for example but not limited to, any non-transitory computer-readable medium, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CDROM), an optical storage device, a transmission media such as those supporting the Internet or an intranet, or a magnetic storage device. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to wireless, wireline, optical fiber cable, RF, and the like.

Computer program code for carrying out operations of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

What is claimed is:

1. A computer program product comprising:
   a non-transitory computer readable medium retaining program instructions, which instructions when read by a processor, cause the processor to perform:
      obtaining a training dataset, the training dataset comprises a sample of data-points, wherein with respect to each data-point a label is provided;
      training a reliability classifier tool using the training dataset and predictions made with respect to data-points of the training dataset made by the classifier tool in response to a training session, wherein the training session comprises training the classifier tool with respect to a portion of the training dataset;
      obtaining a prediction of a label for a dataset made by a classifier tool, wherein the classifier tool is aimed at predicting the label based on a classification model and in view of a set of features defining the dataset;
      obtaining a reliability prediction of a reliability label for the prediction based on the reliability classifier tool, wherein the reliability classifier tool is aimed at predicting the reliability label based on a classification model and in view of a second set of features, wherein the second set of features comprises at least one feature that is not comprised by the set of features and at least one feature that is comprised by the set of features; and
      outputting, at the same stage, to a user the label prediction and the reliability label which indicates a reliability of the label prediction.

2. The computer program product of claim 1, wherein said training comprises:
   repeatedly performing a training session for the classifier tool and determining by the classifier tool predicted labels for the sample of data-points or portion thereof, wherein trained information is not retained by the classifier tool from one training session to another; and
   based on a plurality of predicted labels with respect to a same data-point, training the reliability classifier to predict reliability of prediction by the classifier tool.

3. The computer program product of claim 2, wherein said training the reliability classifier based on the plurality of predicted labels comprises:
   determining a stability measurement based on a variation in the predicted labels with respect to the same data-point; and
   utilizing the stability measurement as a measured reliability of the data-point when training the reliability classifier tool.

4. The computer program product of claim 2, wherein said training the reliability classifier based on the plurality of predicted labels comprises:
   determining a correct fraction of the predicted labels based on a number of times the predicted label for the data-point is substantially equal to the label provided by the training dataset; and
   utilizing the correct fraction measurement as a measured reliability of the data-point when training the reliability classifier tool.

5. The computer program product of claim 1, wherein said training comprises:
   training the classifier tool based on the training dataset and associated labels;
   obtaining predictions by the classifier tool with respect to at least a portion of the dataset; and
   training the reliability classifier tool based on the training dataset and correlation between the predicted label and the associated label with respect to the same data-point.

6. The computer program product of claim 5, wherein said training the classifier is performed with respect to a portion of the training dataset and said obtaining predications is performed with respect to a different portion of the training dataset.

7. The computer program product of claim 5,
   wherein said obtaining predictions comprises, for each data-point in the portion of the dataset:
      obtaining a data-point from the training dataset; and
      introducing the set of features of the data-point to the classifier tool and obtaining a predicted label; and
   wherein said training the reliability classifier tool comprises:
      determining whether the predicted label is different than the associated label in the training dataset, whereby an indication to reliability of the classifier tool's prediction is provided; and
      introducing to the reliability classifier the second set of features with respect to the data-point along with the indication.

8. The computer program product of claim 1, wherein the prediction is relatively unreliable due to the classification model of the classifier tool; and wherein the reliability classifier tool is able to predict the relative unreliability due to being based on a different classification model than the classifier tool.

9. The computer program product of claim 1, wherein said which instructions, when read by a processor, further cause the processor to obtain a probability that the predicted label is correct; and wherein said outputting further provides outputting the probability to the user in addition to the reliability prediction.

* * * * *